United States Patent [19]

Kaidash et al.

[11] Patent Number: 4,576,605
[45] Date of Patent: Mar. 18, 1986

[54] CARDIAC VALVE PROSTHESIS

[75] Inventors: Arnold N. Kaidash; Naum A. Iofis; Semen G. Khurtsilava; Alexandr S. Bukatov; Zinaida P. Danilova, all of Moscow, U.S.S.R.

[73] Assignee: Nauchno-Issledovatelsky Institut Khirurgii Imeni A.V. Vishnevskogo, Moscow, U.S.S.R.

[21] Appl. No.: 707,145

[22] Filed: Mar. 1, 1985

[51] Int. Cl.[4] .............................................. A61F 2/24
[52] U.S. Cl. ...................................................... 623/2
[58] Field of Search .................. 3/1.5; 128/334; 604/8, 604/175

[56] References Cited

U.S. PATENT DOCUMENTS

| Re. 31,040 | 9/1982 | Possis | 3/1.5 |
|---|---|---|---|
| 3,130,419 | 4/1964 | Edwards | 3/1.5 |
| 3,365,728 | 1/1968 | Edwards et al. | 3/1.5 |
| 3,396,409 | 8/1968 | Melrose | 3/1.5 |
| 3,579,645 | 5/1971 | Bokros | 3/1.5 |
| 3,744,060 | 7/1973 | Bellhouse et al. | 3/1.5 |
| 4,042,979 | 8/1977 | Angell | 3/1.5 |
| 4,106,129 | 8/1978 | Carpentier et al. | 3/1.5 |
| 4,164,046 | 8/1979 | Cooley | 3/1.5 |

FOREIGN PATENT DOCUMENTS

| 1388064 | 3/1975 | United Kingdom . | |
| 0848024 | 7/1981 | U.S.S.R. | 3/1.5 |

Primary Examiner—Richard J. Apley
Assistant Examiner—Alan W. Cannon
Attorney, Agent, or Firm—Fleit, Jacobson, Cohn & Price

[57] ABSTRACT

A cardiac valve prosthesis including an annular body having a valving member and a suturing collar. The collar has a V-shaped groove in which is mounted a movable disc segment intended for covering calcinosis. There is provided a cord for retaining the disc segment in a desired angular position relative to the suturing collar.

3 Claims, 3 Drawing Figures 4,576,605

CARDIAC VALVE PROSTHESIS

TECHNICAL FIELD

This invention relates to the field of medicine, and more particularly, to the field of cardiosurgery; more specifically, the invention relates to a cardiac valve prosthesis that may be used for remedying valvular afflictions accompanied by calcinosis, and to isolate the latter.

BACKGROUND ART

Known in the art is a cardiac valve prosthesis comprising an annular body with a disc valving member made of a biologically inert material. A suturing collar is disposed outside the annular body, on the periphery thereof, for attaching the cardiac valve prosthesis within the cardiac cavity. The collar is also made of a biologically inert material and is in the form of a ring which is to be sutured to the surrounding tissues (cf. U.S. Pat. No. 4,106,129).

This known design of a cardiac valve prosthesis is deficient in that it cannot be used for remedying valvular afflictions complicated with calcinosis by isolating the calcinosis simultaneously with providing the benefits of the cardiac valve prosthesis.

SUMMARY OF THE INVENTION

An object of the invention is to provide a cardiac valve prosthesis which would make it possible to isolate calcinosis simultaneously with providing the benefits of the cardiac valve prosthesis.

The foregoing and other objects are accomplished by providing a cardiac valve prosthesis comprising an annular body having a valving member and a suturing collar disposed outside the annular body. According to the invention, the suturing collar has a groove extending along the entire outer circumference thereof, and a disc segment made of an elastic material is mounted in said groove, which disc segment is angularly adjustable about an axis extending at right angles to the plane of the suturing collar, and is retainable in the adjusted position.

The advantage of the cardiac valve prosthesis according to the invention resides in the fact that it provides for the possibility of isolating calcinosis without removing it during the process of implantation of the cardiac valve prosthesis, owing to the covering of the calcinosis by the disc segment. It should be noted that, owing to the fact that the disc segment is adjustable relative to the suturing collar, calcinosis can be covered irrespective of its position with respect to the cardiac valve prosthesis being implanted.

Generally speaking, the groove in the suturing collar may be of any desired cross-sectional configuration, but experience has shown that the best implantation is ensured when the groove in the cross-section is V-shaped.

A fastening cord is preferably provided on the inner concave periphery of the disc segment, the ends of the cord being connected together by a knot tied in the cord for retaining the disc segment with respect to the prosthetic valve body.

BRIEF DESCRIPTION OF THE DRAWINGS

The invention will now be described with reference to a specific non-limiting example of its practical realization, illustrated in the accompanying drawings, in which.

Figure 1:
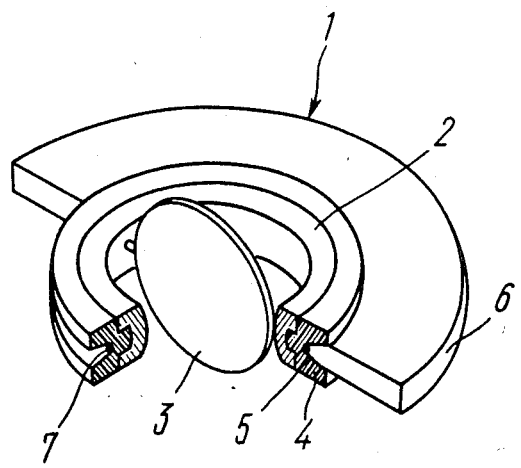
FIG. 1 is a perspective view, partially in section, of a cardiac valve prosthesis according to the invention.

A cardiac valve prosthesis, generally designated at 1 in FIG. 1, comprises an annular body 2 having a disc or any other valving member 3 of any appropriate known type, and valve stroke limiters (not shown in FIG. 1 for the sake of clarity so as not to show details that have no material bearing on the invention) which also may be of a biologically inert material.

Figure 2:
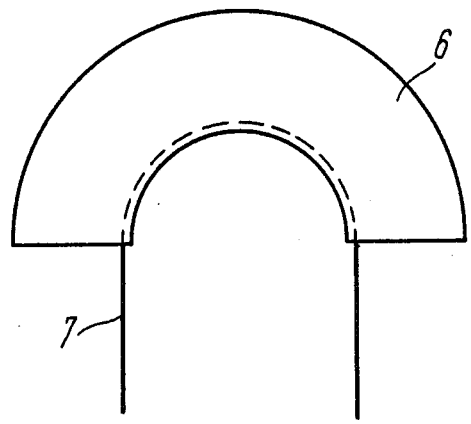
FIG. 2 is a plan view of a disc segment of a cardiac valve prosthesis according to the invention.

A suturing collar 4 made of a biologically inert material is disposed on the outer surface of the body 2 along the entire outer circumference thereof and is secured to the body by any appropriate known method. As can be clearly seen in FIG. 1, the suturing collar 4 has a groove 5 of a V-shaped cross-sectional configuration extending along the entire outer circumference of the collar 4. A disc segment 6, shown individually in FIG. 2, is mounted in the groove 5 for angular adjustment about an axis extending at right angles to the plane of the suturing collar. The disc segment 6 should be made of a biologically inert material such as, for example, the material of the collar 4, and, at the same time, it should be elastic. For retaining the disc segment 6 in the groove in the desired adjusted position with respect to the body 2, a cord 7 is provided which extends over the inner concave side of the disc segment.

Figure 3:
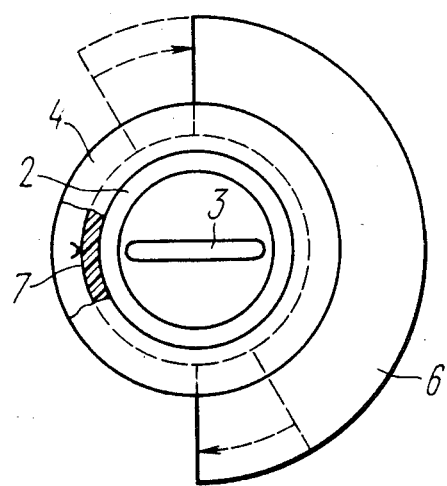
FIG. 3 is a top view of a complete cardiac valve prosthesis according to the invention.

FIG. 3 shows the disc segment in position on the prothesis, the dashed lines representing one angular position thereof and the solid lines representing another angular position, the cord 7 being tied in a knot to hold the disc segment in place.

The implantation of the cardiac valve prosthesis in the case of an operation for replacing a cardiac valve affected by massive calcinosis will now be described.

As usual, the thoracic cavity, the pericardium cavity and the cardiac cavity are opened by any appropriate known method used for cardiac operations. The valve being replaced is excised and the valve prosthesis is implanted to replace the excised valve using any known technique. The disc segment 6 is angularly displaced in the groove of the collar 4, about an axis extending at right angles to the plane of the suturing collar, so that the segment 6 can be disposed within the zone of calcinosis, whereafter the ends of the cord 7 are tied to form a knot at a position of the suturing collar 4 opposite the remotest point of the outer convex periphery of the segment 6, thereby fixing the disc segment 6 in the desired position, by using the elasticity of the material of the segment 6, the segment is deformed so as to place it over the calcinosis. The excessive part, i.e., the part which extends beyond the calcinosis, is cut off, and the remaining part is fixed to the healthy, unaltered tissues with a continuous suture.

The use of the invention eliminates the appearance of paravalvular fistulae, improves reliability of operation and reduces operation time.

What is claimed is:

1. In a cardiac valve prosthesis including an annular body having a valving member and an annular suturing collar disposed outside the annular body, the improvement comprising an annular suturing collar having an outer periphery and a groove extending along the entire outer periphery thereof, and a disc segment made of an elastic material, said disc segment mounted in said groove for angular displacement therewithin relative to the axis of the suturing collar to permit positioning of said disc segment in a desired angular position.

2. A valve prosthesis according to claim 1, in which the groove is of a V-shaped cross-section.

3. A valve prosthesis according to claim 1, in which a fastening cord is provided on an inner periphery of the disc segment, the cord having ends extending outwardly of said disc segment for connection together to form a knot for retaining the disc segment in a desired angular position relative to the annular body of the valve prosthesis.

* * * * *